United States Patent [19]
O'Lenick, Jr.

[11] Patent Number: 5,650,529
[45] Date of Patent: Jul. 22, 1997

[54] SILICONE ESTER AMINO COMPOUNDS

[75] Inventor: Anthony J. O'Lenick, Jr., Lilburn, Ga.

[73] Assignee: Siltech Inc., Norcross, Ga.

[21] Appl. No.: 744,261

[22] Filed: Nov. 6, 1996

Related U.S. Application Data

[63] Continuation-in-part of Ser. No. 642,936, May 6, 1996, Pat. No. 5,591,880.

[51] Int. Cl.$^6$ .................................................. C07F 7/10
[52] U.S. Cl. ................................................................ 556/418
[58] Field of Search ................................................ 556/418

[56] References Cited

U.S. PATENT DOCUMENTS

| | | | |
|---|---|---|---|
| 3,338,943 | 8/1967 | Speier | 556/418 |
| 3,511,699 | 5/1970 | Johnson et al. | 117/135.5 |
| 3,558,556 | 1/1971 | Berger et al. | 556/418 X |
| 4,548,842 | 10/1985 | Pohl | 556/418 X |
| 5,516,869 | 5/1996 | Lucarelli et al. | 556/418 X |

*Primary Examiner*—Paul F. Shaver

[57] ABSTRACT

The invention discloses novel silicone compounds which contain an amino group on the molecule, and an ester linkage between the two. Compounds of the invention are made by reacting (a) a carboxy silicone, and (b) a hydroxy containing tertiary amine. Compounds may also contain a polyoxyalkylene group. Compounds of the invention by virtue of (i) the silicone group, (ii) the ester group and (iii) the amino group are extremely efficient softeners.

17 Claims, No Drawings

SILICONE ESTER AMINO COMPOUNDS

BACKGROUND OF THE INVENTION

1. Related Application

This application is a continuation in part of application Ser. No. 08/642,936, filed May 6, 1996, U.S. Pat. No. 5,591,880.

2. Field of the Invention

The invention discloses novel silicone compounds which contain an amino group on the molecule, and an ester linkage between the two. Compounds of the invention are made by reacting (a) a carboxy silicone, and (b) a hydroxy containing tertiary amine. Compounds may also contain a polyoxyalkylene group. Compounds of the invention by virtue of (i) the silicone group, (ii) the ester group and (iii) the amino group are extremely efficient softeners.

The reaction used to prepare the compounds of the present invention is an esterification of a carboxy silicone which may contain varying amounts of polyoxyalkylene in the molecule, and a tertiary amine containing a single hydroxyl group.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts to overcome this deficiency have been made by reacting stearyl alcohol with a chlorosilane. The difficulty with the use of this type of material is that a large excess (50% by weight) of the alcohol needs to be added to get a product which is free of the irritating chlorosilane raw material. When such an excess is used the product behaves functionally more like the stearyl alcohol than like a silicone compound.

Additionally, the compound is not polymeric, hence the superior lubrication and hydrophobicity enhancements which can be achieved by dimethylpolysiloxane is not obtainable with these compounds.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

OBJECT OF THE INVENTION

It is the object of the present invention to provide textile which are effective at very low concentrations, do not yellow and do not persist in the environment. The structural components of the invention allow for the preparation of a molecule which has the desired properties. The presence of silicone in the molecule gives superior softening, the presence of the tertiary amine gives superior softening and lubrication and the introduction of the ester linkage between the silicone and tertiary amine results in a linkage which will biodegrade rapidly in waste water, making the compound less persistent in the waste water stream.

The formation of the ester linkage and the incorporation of the amino group into the silicone of the present invention is accomplished by an esterification reaction of a carboxy silicone and a hydroxy tertiary amine.

The application from which this application is a continuation in part is based upon alkoxylated carboxy compounds. The selection of the hydrophobic carboxy compounds of the present invention results in hydrophobic softeners rather than the hydrophilic products which result from the technology used to make the compounds of the parent application.

SUMMARY OF THE INVENTION

The invention discloses novel silicone compounds which contain an amino group on the molecule, and an ester linkage between the two. Compounds of the invention are made by reacting (a) a carboxy silicone, and (b) a hydroxy containing tertiary amine. Compounds may also contain a polyoxyalkylene group. Compounds of the invention by virtue of (i) the silicone group, (ii) the ester group and (iii) the amino group are extremely efficient softeners.

The compounds of this invention are made by the esterification of a carboxy silicone compound and a hydroxy containing tertiary amine. In order to obtain a molecule with the desired attributes, each functional group needs to be exact. In order to make the ester, the amino compound must be mono-hydroxyl. This prevents crosslinking with the carboxy silicone, and formation of a polyester. The polyester is undesirable. The second requirement is that the amine must be tertiary. Tertiary amines do not react with carboxy compounds to form amides. If a primary or secondary amine were substituted, amide would form and the substantivity of the amino compound would be destroyed. In addition if a non-tertiary amine were used, a combination the ester and amide would form, making polymeric products.

Only if the compounds are specifically selected will compounds useful in the preparation of the compounds of the present invention be obtained.

Specifically, the compounds of the present invention are esters compounds which is prepared by the esterification reaction of;

(a) a silicone carboxylate conforming to the following structure:

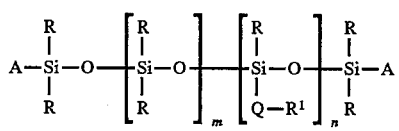

wherein:
R is methyl;
$R^1$ is H;
Q is a $-(CH_2)_c-C(O)-O-$;
c is an integer ranging from 3 to 17;
A is selected from $-R$ or $-Q-R^1$,
m is an integer ranging from 1 to 200;
n is an integer ranging 0 to 10 when A is $-Q-R^1$, and an integer ranging from 1 to 10 when A is R; and
(c) a tertiary amine conforming to the following structure:

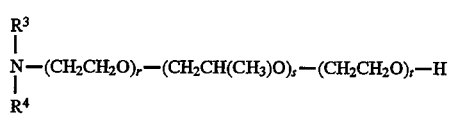

wherein;
$R^3$ and $R^4$ are independently $CH_3-(CH_2)k-$;
k is an integer ranging from 0 to 20;
r, s and t are independently integers ranging from 0 to 20, with the proviso that r+s+t be greater than 1.

Compounds of the present invention conform to the following structure:

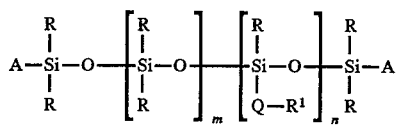

wherein:
R is methyl;
$R^1$ is;

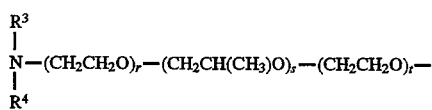

Q is a $-(CH_2)_c-C(O)-O-$;
c is an integer ranging from 3 to 17;
A is selected from $-R$ or $-Q-R^1$,
m is an integer ranging from 1 to 200;
n is an integer ranging 0 to 10 when A is $-Q-R^1$, and an integer ranging from 1 to 10 when A is R;
$R^3$ and $R^4$ are independently $CH_3-(CH_2)k-$;
k is an integer ranging from 0 to 20;
r, s and t are independently integers ranging from 0 to 20, with the proviso that r+s+t be greater than 1.

EXAMPLES

The compounds of the present invention are prepared by the reaction of a carboxy silicone compound and a monohydroxy containing tertiary amine. Examples of suitable reactants are as follows;

All percentages given are based upon percent by weight, based upon the total weight of the entire batch. All temperatures are degrees C.

Reactants

Hydroxy Amines

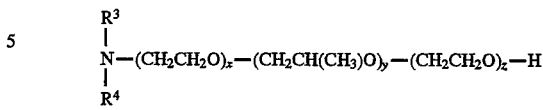

wherein;
$R^3$ and $R^4$ are independently $CH_3-(CH_2)k-$;
k is an integer ranging from 0 to 20;
x, y and z are independently integers ranging from 0 to 20, with the proviso that x+y+z be greater than 1.

| Reactant Example Number | $R^3$ | $R^4$ | x | y | z |
| --- | --- | --- | --- | --- | --- |
| 1 | $CH_3$ | $CH_3$ | 1 | 0 | 0 |
| 2 | $CH_3$ | $CH_3$ | 10 | 10 | 10 |
| 3 | $CH_3CH_2$ | $CH_3CH_2$ | 10 | 5 | 0 |
| 4 | $CH_3CH_2$ | $CH_3CH_2$ | 0 | 0 | 1 |
| 5 | $CH_3$ | $CH_3$ | 10 | 5 | 10 |
| 6 | $CH_3(CH_2)_{11}$ | $CH_3(CH_2)_{11}$ | 20 | 20 | 20 |
| 7 | $CH_3(CH_2)_{19}$ | $CH_3(CH_2)_{19}$ | 0 | 0 | 1 |
| 8 | $CH_3(CH_2)_{13}$ | $CH_3(CH_2)_{13}$ | 0 | 1 | 0 |

Carboxy Functional Silicone Compounds

Many manufacturers offer a series of carboxy functional silicone compounds suitable for use as raw materials in the preparation of the esters of the present invention. These materials are marketed under the many trade names. Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art. Compounds conform to the following structure;

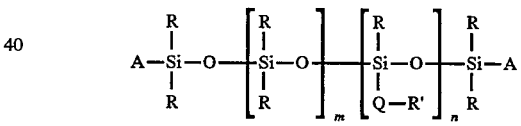

Wherein R is methyl;
R' is $-H$;
Q is $(CH_2)_c-C(O)-O-$;
c is an integer from 3 to 17;
A is methyl;
m is an integer ranging from 1 to 200;
n is an integer ranging 0 to 10 when A is $-Q-R^1$, and an integer ranging from 1 to 10 when A is R;

| Example | Name | c | n | m |
| --- | --- | --- | --- | --- |
| 9 | Siltech C 1000 | 10 | 3 | 15 |
| 10 | Siltech C 1100 | 10 | 1 | 20 |
| 11 | Siltech C 1200 | 3 | 4 | 50 |
| 12 | Siltech C 1300 | 3 | 2 | 200 |
| 13 | Siltech C 1400 | 4 | 1 | 29 |
| 14 | Siltech C 1500 | 17 | 3 | 1 |
| 15 | Siltech C 1600 | 17 | 4 | 150 |
| 16 | Siltech C 1700 | 4 | 10 | 55 |

Terminal Substituted Carboxy Functional Silicone

Terminal substituted carboxy functional silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

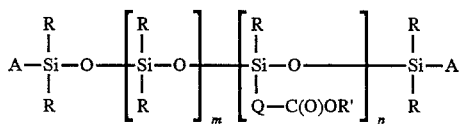

Wherein R is methyl;
R' is —H;
Q is $(CH_2)_c$—c(O)—O—;
c is an integer from 3 to 17;
n is 0;
A is —Q—R';

| Example | Name | c | m |
|---|---|---|---|
| 17 | Siltech CT 701 | 10 | 1 |
| 18 | Siltech CT 706 | 3 | 200 |
| 19 | Siltech CT 710 | 17 | 50 |
| 20 | Siltech CT 750 | 10 | 100 |
| 21 | Siltech CT 790 | 3 | 150 |

Compounds of the Present Invention

General Reaction Conditions;

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

General Procedure

Into a suitable round bottom, three neck flask equipped with a Dean Stark trap, a thermometer and a nitrogen sparge is added the specified number of grams of the carboxy silicone and the specified number of grams of hydroxyamino compound and 0.25 % of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 22

Into a suitable round bottom, three neck flask equipped with a Dean Stark trap, a thermometer and a nitrogen sparge is added the specified number of grams of the carboxy silicone), 74.0 grams of example 9, and 80.0 grams of the hydroxy amine (example 1) and 0.25 % of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 23–50

Example 22 is repeated only this time substituting the specified number of grams of the specified carboxy silicone for the carboxy silicone specified and the specified type and the specified type and number of grams of hydroxy amine as shown below;

| | Hydroxy Amine | | Carboxy Compounds | |
|---|---|---|---|---|
| Example | Example | Grams | Example | Grams |
| 23 | 1 | 89.0 | 9 | 609.0 |
| 24 | 2 | 1515.0 | 10 | 1827.0 |
| 25 | 3 | 808.0 | 11 | 1051.0 |
| 26 | 4 | 117.0 | 12 | 7570.0 |
| 27 | 5 | 1220.0 | 13 | 2409.0 |
| 28 | 6 | 3293.0 | 14 | 361.0 |
| 29 | 7 | 621.0 | 15 | 3100.0 |
| 30 | 8 | 468.0 | 16 | 524.2 |
| 41 | 1 | 89.0 | 17 | 290.0 |
| 42 | 2 | 1515.0 | 18 | 7553.0 |
| 43 | 3 | 808.0 | 19 | 2200.0 |
| 44 | 4 | 117.0 | 20 | 4000.0 |
| 45 | 5 | 1220.0 | 21 | 5700.0 |
| 46 | 6 | 3293.0 | 20 | 4000.0 |
| 47 | 7 | 621.0 | 19 | 2200.0 |
| 48 | 8 | 468.0 | 18 | 7553.0 |
| 49 | 1 | 89.0 | 17 | 209.0 |
| 50 | 2 | 1515.0 | 16 | 524.2 |

The compounds of the present invention are hydrophobic softeners which have excellent hand on textile fibers and fabrics.

What is claimed:

1. A compound prepared by the esterification reaction of;
   (a) a silicone carboxylate conforming to the following structure:

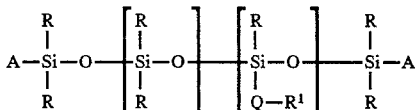

wherein:
R is methyl;
$R^1$ is H;
Q is a —$(CH_2)_c$—C(O)—O—;
c is an integer ranging from 3 to 17;
A is selected from —R or —Q—$R^1$,
m is an integer ranging from 1 to 200;
n is an integer ranging 0 to 10 when A is —Q—$R^1$, and an integer ranging from 1 to 10 when A is R; and
   (c) a tertiary amine conforming to the following structure:

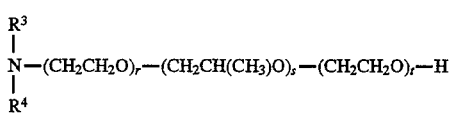

wherein;

$R^3$ and $R^4$ are independently $CH_3—(CH_2)k-$;

k is an integer ranging from 0 to 20;

r, s and t are independently integers ranging from 0 to 20, with the proviso that r+s+t be greater than 1.

2. A compound of claim 1 wherein A is $—Q—R^1$.
3. A compound of claim 1 wherein A is R.
4. A compound of claim 2 wherein k is 0.
5. A compound of claim 3 wherein k is 0.
6. A compound of claim 2 wherein k is 1.
7. A compound of claim 3 wherein k is 1.
8. A compound of claim 2 wherein said esterification reaction is conducted at between 140 and 240 C.
9. A compound of claim 3 wherein said esterification reaction is conducted at between 180 and 200 C.
10. A compound conforming to the following structure:

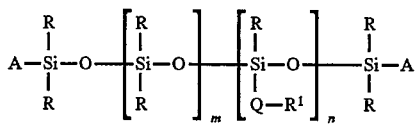

wherein:

R is methyl;

$R^1$ is;

$$\begin{array}{c} R^3 \\ | \\ N—(CH_2CH_2O)_r—(CH_2CH(CH_3)O)_s—(CH_2CH_2O)_t— \\ | \\ R^4 \end{array}$$

Q is a $—(CH_2)_c—C(O)—O—$;

c is an integer ranging from 3 to 17;

A is selected from $—R$ or $—Q—R^1$, m is an integer ranging from 1 to 200;

n is an integer ranging 0 to 10 when A is $—Q—R^1$, and an integer ranging from 1 to 10 when A is R;

$R^3$ and $R^4$ are independently $CH_3—(CH_2)k-$;

k is an integer ranging from 0 to 20;

r, s and t are independently integers ranging from 0 to 20, with the proviso that r+s+t be greater than 1.

11. A compound of claim 10 wherein A is $—Q—R^1$.
12. A compound of claim 10 wherein A is R.
13. A compound of claim 11 wherein A is $—Q—R^1$.
14. A compound of claim 12 wherein k is 0.
15. A compound of claim 11 wherein k is 0.
16. A compound of claim 12 wherein k is 1.
17. A compound of claim 12 wherein k is 1.

* * * * *